(12) United States Patent
Piltch et al.

(10) Patent No.: US 9,110,024 B2
(45) Date of Patent: Aug. 18, 2015

(54) FIBER OPTICAL ASSSEMBLY FOR FLUORESCENCE SPECTROMETRY

(75) Inventors: Martin S. Piltch, Los Alamos, NM (US); Perry Clayton Gray, Los Alamos, NM (US); Richard Rubenstein, Staten Island, NY (US)

(73) Assignee: Los Alamos National Security, LLC, Los Alamos, NM (US)

( * ) Notice: Subject to any disclaimer, the term of this patent is extended or adjusted under 35 U.S.C. 154(b) by 428 days.

(21) Appl. No.: 13/258,727

(22) PCT Filed: Mar. 25, 2010

(86) PCT No.: PCT/US2010/028692
§ 371 (c)(1),
(2), (4) Date: Jan. 5, 2012

(87) PCT Pub. No.: WO2010/111508
PCT Pub. Date: Sep. 30, 2010

(65) Prior Publication Data
US 2012/0112069 A1    May 10, 2012

Related U.S. Application Data

(60) Provisional application No. 61/211,264, filed on Mar. 25, 2009.

(51) Int. Cl.
*G01N 21/64* (2006.01)
*G01N 33/00* (2006.01)
(Continued)

(52) U.S. Cl.
CPC .............. *G01N 21/645* (2013.01); *G01N 21/65* (2013.01); *G01N 33/4833* (2013.01); *G01N 2021/6467* (2013.01); *G01N 2021/6484* (2013.01)

(58) Field of Classification Search
CPC .............. G01N 2021/6467; G01N 2021/6484; G01N 21/645; G01N 21/65; G01N 33/4833
USPC .............. 250/458.1, 459.1; 356/317, 318, 417
See application file for complete search history.

(56) References Cited

U.S. PATENT DOCUMENTS 4,702,598 A    10/1987   Bohmer
5,714,388 A     2/1998   Kusnetz
(Continued)

FOREIGN PATENT DOCUMENTS

CN        1444726 A    9/2003
CN      101194159 A    6/2008
(Continued)

OTHER PUBLICATIONS

Atarashi, et al., "Simplified Ultrasensitive Prion Detection by Recombinant PrP Conversion with Shaking," Nature Methods 5(3), Mar. 2008, pp. 211-212.
(Continued)

*Primary Examiner* — Mark R Gaworecki
(74) *Attorney, Agent, or Firm* — Baker & Hostetler LLP

(57) ABSTRACT

System is provided for detecting the presence of an analyte of interest in a sample, said system comprising an elongated, transparent container for a sample; an excitation source in optical communication with the sample, wherein radiation from the excitation source is directed along the length of the sample, and wherein the radiation induces a signal which is emitted from the sample; and, at least two linear arrays disposed about the sample holder, each linear array comprising a plurality of optical fibers having a first end and a second end, wherein the first ends of the fibers are disposed along the length of the container and in proximity thereto; the second ends of the fibers of each array are bundled together to form a single end port.

12 Claims, 5 Drawing Sheets

(51) Int. Cl.
  *G01N 21/65* (2006.01)
  *G01N 33/483* (2006.01)

(56) References Cited

U.S. PATENT DOCUMENTS

| | | | |
|---|---|---|---|
| 6,124,597 | A | 9/2000 | Shehada et al. |
| 6,538,735 | B1 | 3/2003 | Duebendorfer et al. |
| 7,041,807 | B1 | 5/2006 | Cashman et al. |
| 7,079,252 | B1 | 7/2006 | Debreczeny et al. |
| 7,777,869 | B2 | 8/2010 | Nerin et al. |
| 7,847,941 | B2 | 12/2010 | Carpenter |
| 2002/0001075 | A1 | 1/2002 | Tsien et al. |
| 2003/0116436 | A1 | 6/2003 | Amirkhanian et al. |
| 2003/0127609 | A1 | 7/2003 | El-Hage et al. |
| 2003/0191398 | A1 | 10/2003 | Motz et al. |
| 2004/0073120 | A1 | 4/2004 | Motz et al. |
| 2006/0263767 | A1 | 11/2006 | Castrillon et al. |
| 2007/0251337 | A1 | 11/2007 | Reed et al. |
| 2010/0261195 | A1 | 10/2010 | Rubenstein et al. |

FOREIGN PATENT DOCUMENTS

| | | |
|---|---|---|
| CN | 101299024 A | 11/2008 |
| EP | 0824211 | 2/1998 |
| JP | 10-90187 | 4/1998 |
| WO | WO 00/78344 A1 | 12/2000 |
| WO | WO 2010/111514 A1 | 9/2010 |

OTHER PUBLICATIONS

Bieschke, et al., "Autocatalytic Self-Propagation of Misfolded Prion Protein," Proceedings of the National Academy of Sciences 101(33), Aug. 17, 2004, pp. 12207-12211.

Brown, et al., "Conservation of Infectivity in Purified Fibrillary Extracts of Scrapie-Infected Hamster Brain After Sequential Enzymatic Digestion or Polyacrylamide Gel Electrophoresis," Proceedings of the National Academy of Sciences 87, Sep. 1990, pp. 7240-7244.

Brown, et al., "Normal Prion Protein has an Activity Like That of Superoxide Dismutase," Biochemistry Journal 344, 1999, pp. 1-5.

Bueler, et al., "High Prion and PrPSc Levels But Delayed Onset of Disease in Scrapie-Inoculated Mice Heterogenzygous for a Disrupted PrP Gene," Molecular Medicine, 1994, pp. 19-30.

Carlson, et al., "Prion Isolate Specified Allotypic Interactions Between the Cellular and Scrapie Prion Proteins in Congenic and Transgenic Mice," Proceedings of the National Academy of Sciences 91, Jun. 1994, pp. 5690-05694.

Castilla, et al., "Detection of Prions in Blood," Nature Medicine 11(9), Sep. 2005, pp. 982-985.

Castilla, et al., "In Vitro Generation of Infectious Scrapie Prions," Cell 121, Apr. 22, 2005, pp. 195-206.

Chang, et al., "PrP Antibody Binding-Induced Epitope Modulation Evokes Immunocooperativity," Journal of Neuroimmunology 205, Sep. 2008, pp. 94-100.

Chang, et al., "Surround Optical Fiber Immunoassay (SOFIA): An Ultra-Sensitive Assay for Prion Protein Detection," Journal of Virological Methods, Feb. 27, 2009, 159(1), pp. 15-22.

Deleault, et al., "Protease-Resistant Prion Protein Amplification Reconstituted with Partially Purified Substrates and Synthetic Polyanions," Journal of Biological Chemistry 280(29), Jul. 22, 2005, pp. 26873-26879.

European Patent Application No. EP 10 75 6857: Extended European Search Report dated Aug. 21, 2012, 14 pages.

Gavier-Widen, et al., "Diagnosis of Transmissible Spongiform Encephalopathies in Animals: A Review," Journal of Veterinary Diagnostic Investigation 17, 2005, pp. 509-527.

Gossner et al., "Role of lymph-borne cells in the early stages of scrapie agent dissemination from the skin", Veterinary Immunology and Immunopathology, Feb. 15, 2006, 109(3-4), 267-278.

Haley, et al., "Detection of CWD Prions in Urine and Saliva of Deer by Transgenic Mouse Bioassay," PLoS One 4, Mar. 18, 2009, pp. e4848.

Haley, et al., "Detection of Sub-Clinical CWD Infection in Conventional Test-Negative Deer Long After Oral Exposure to Urine and Feces from CWD+ Deer," PLoS One 4, Nov. 24, 2009, p. e7990.

Hilmert, et al., "A Rapid and Efficient Method to Enrich SAF-Protein from Scrapie Brains of Hamsters," Bioscience Reports 4, Jan. 10, 1984, pp. 165-170.

Houston, et al., "Transmission of BSE by Blood Transfusion in Sheep," Lancet 356, Sep. 16, 2000, pp. 999-1000.

International Patent Application No. PCT/US2010/028692: International Search Report and Written Opinion dated May 27, 2010, 9 pages.

International Patent Application No. PCT/US2010/028698: International Search Report dated Aug. 11, 2010, 4 pages.

International Patent Application No. PCT/US2010/028698: Written Opinion dated Jul. 22, 2010, 7 pages.

Jones, et al., "In Vitro Amplification and Detection of Variant Creutzfeldt-Jakob Disease PrP(Sc)," Journal of Pathology 213, May 2007, pp. 21-26.

Jones, et al., "Preferential Cu2+ Coordination by His96 and His111 Induces Beta-sheet Formation in the Sunstructured Amyloidogenic Region of Prion Protein," Journal of Biological Chemistry 279(31), Jul. 30, 2004, pp. 32018-32027.

Kang, et al., "Guanidine Hydrochloride Extraction and Detection of Prion Proteins in Mouse and Hamster Prion Diseases by ELISA," Journal of Pathology 199, Feb. 3, 2003, pp. 534-541.

Kascsak, et al., "Immunological Comparison of Scrapie-Associated Fibrils Isolated from Animals Infected with Four Different Scrapie Strains," Journal of Virology 59(3), Sep. 1986, pp. 676-683.

Kascsak, et al., "Mouse Polyclonal and Monoclonal Antibody to Scrapie-Associated Fibril Proteins," Journal of Virology 61(12), Dec. 1987, pp. 3688-3698.

Kim, et al., "Comparison of PrP Transcription and Translation in Two Murine Myeloma Cell Lines," Journal of Neuroimmunology, 140, May 2, 2003, pp. 137-142.

Kocisko, et al., "Cell-Free Formation of Protease-Resistant Prion Protein," Nature 370, Aug. 11, 1994, pp. 471-474.

Kurt, et al., "Efficient In Vitro Amplification of Chronic Wasting Disease PrPres," Journal of Virology 81(17), Sep. 2007, pp. 9605-9608.

LaFauci, et al., "Passage of Chronic Wasting Disease Prion into Transgenic Mice Expressing Rocky Mountain Elk (*Cereus elaphus nelsoni*) PrPC," Journal of General Virology 87, Aug. 2006, pp. 3773-3780.

Lau, et al., "Characterization of Prion Protein (PrP)-Derived Peptides the Discriminate Dull-length PrPSc from PrPc," PNAS, 2007, 104(28), pp. 11551-11556.

Llewelyn, et al., "Possible Transmission of Variant CJD Disease by Blood Transfusion," Lancet 363(9407), Feb. 7, 2004, pp. 417-421.

Madec, et al., "Abnormal Prion Protein in Genetically Resistant Sheep from a Scrapie-Infected Flock," Journal of General Virology 85, Jul. 2004, pp. 3483-3486.

Mathiason, et al., "Infectious Prions in Pre-Clinical Deer and Transmission of Chronic Wasting Disease Solely by Environmental Exposure," PLoS One 4, Jun. 16, 2009, e5916.

Mathiason, et al., "Infectious Prions in the Saliva and Blood of Deer with Chronic Wasting Disease," Science 314, Oct. 6, 2006, p. 133-136.

Murayama, et al., Urinary Excretion and Blood Level of Prions in Scrapie-Infected Hamsters, Journal of General Virology 88, Jun. 8, 2007, pp. 2890-2898.

Peden, et al., "Preclinical vCJD After Blood Transfusion in a PRNP Codon 129 Heterozygous Patient," Lancet 264, Aug. 7, 2004, pp. 527-529.

Prusiner, et al., "Transgenic Studies Implicate Interactions Between Homologous PrP Isoforms in Scrapie Prion Replication," Cell 63, Nov. 16, 1990, pp. 673-686.

Raymond, et al., "Evidence of a Molecular Barrier Limiting Susceptibility of Humans, Cattle, and Sheep to Chronic Wasting Disease," EMBO Journal 19(17), Jul. 5, 2000, pp. 4425-4430.

(56) References Cited

OTHER PUBLICATIONS

Rubenstein, et al., "Concentration and Distribution of Infectivity and PrPSc Following Partial Denaturation of a Mouse-Adapted and a Hamster-Adapted Scrapie Strain," Archives of Virology 139, Aug. 16, 1994, pp. 301-311.

Saa, et al., "Presymptomatic Detection of Prions in Blood," Science 313, Jul. 7, 2006, pp. 92-94.

Saborio, et al., "Sensitive Detection of Pathological Prion Protein by Cyclic Amplification of Protein Misfolding," Nature 411, Jun. 14, 2001, pp. 810-813.

Soto, et al., Pre-Symptomatic Detection of Prions by Cyclic Amplification of Protein Misfolding, FEBS Letters 579, Dec. 2004, pp. 638-642.

Tamguney, et al., "Asymptomatic Deer Excrete Infectious Prions in Faeces," Nature 461, Sep. 24, 2009, pp. 529-532.

Tayebi, et al., "Disease-Associated Prion Protein Elicits Immunoglobulin M Responses In Vivo," Molecular Medicine 10(7-13), Jul.-Dec. 2004, pp. 104-111.

Thorne, et al., "In Vitro Amplification of PrPSc Derived From the Brain and Blood of Sheep Infected with Scrapie," Journal of General Virology 89, Aug. 5, 2008, pp. 3177-3184.

Van Keulen, et al., "Immunohistochemical Detection and Localization of Prion Protein in Brain tissue of Sheep with Natural Scrapie," Veterinary Pathology 32(3), 1995, pp. 299-308, downloaded from vet.sagepub.com on Sep. 17, 2010.

Van Keulen, et al., "Immunohistochemical Detection of Prion Protein in Lymphoid Tissues of Sheep with natural Scrapie," Journal of Clinical Microbiology 34(5), May 1996, pp. 1228-1231.

Wild, et al., "Comparison of Growth Rate and Milk Intake of Bottle-Raised and Dam-Raised Bighorn Sheep, Pronghorn Antelope and Elk Neonates," The Journal of Wildlife Management 58(2), Apr. 1994, pp. 340-347.

Wolfe, et al., "PrPCWD in Rectal Lymphoid Tissue of Deer (*Odocoileus* spp.)," Journal of General Virology 88, Mar. 6, 2007, pp. 2078-2082.

Chinese Patent Application No. 201080013299.4: English translation of Office Action and Search Report dated Oct. 23, 2013, 9 pages.

FIBER OPTICAL ASSSEMBLY FOR FLUORESCENCE SPECTROMETRY

STATEMENT REGARDING FEDERAL RIGHTS

This invention was made with government support under Contract No. DE-AC52-06 NA 25396, awarded by the U.S. Department of Energy. The government has certain rights in the invention.

CROSS-REFERENCE TO RELATED APPLICATIONS

This application is the National Stage of International Application No. PCT/US2010/028692 filed Mar. 25, 2010, which claims the benefit of U.S. Provisional Application No. 61/211,264, filed Mar. 25, 2009, the disclosures of which are incorporated herein by reference in their entirety.

BACKGROUND OF INVENTION

The present invention relates generally to an apparatus and method for improved optical geometry for enhancement of spectroscopic detection of analytes in a sample. More particularly, the invention relates to an apparatus and method for ultrasensitive detection of prions and other low-level analytes.

A conventional method of performing laser induced fluorescence as well as other types of spectroscopic measurements such as infrared, UV-vis, phosphorescence, etc. is to use a small transparent cuvette to contain the sample to be analyzed. A standard cuvette has dimensions of about 1 cm×1 cm and is about 3.5 cm in height and sealed at the bottom. The cuvette is usually made of fused quartz or optical quality borosilicate glass, is optically polished and may have an antireflective coating. The cuvette is filled from an upper, open end that may be equipped with a stopper.

To perform a measurement, the cuvette is filled with the liquid to be investigated and then illuminated with a laser focused through one of the cuvette's faces. A lens is placed in line with one of the faces of the cuvette located at ninety degrees from the input window to collect the laser-induced fluorescence light, so as to reduce interference from the laser itself and from other noise. Only a small volume of the cuvette is actually illuminated by the laser and produces a detectable spectroscopic emission. The output signal is significantly reduced by the fact that the lens picks up only approximately ten percent of the spectroscopic emission due to solid angle considerations. This general system has been used for at least seventy-five years.

Previous developments described in U.S. patent application Ser. No. 11/634,546, filed on Dec. 7, 2006, increased the amount of output signal by approximately a factor of ten over the prior art known at the time, resulting in micromolar limits of detection of fluorescent compounds. The present invention further improves upon this technology, and may result in detection of attomolar quantities of fluorescent compounds.

SUMMARY OF INVENTION

The following describe some non-limiting embodiments of the present invention.

According to one embodiment of the present invention, a system is provided for detecting the presence of an analyte of interest in a sample, said system comprising an elongated, transparent container for a sample; an excitation source in optical communication with the sample, wherein radiation from the excitation source is directed along the length of the sample, and wherein the radiation induces a signal which is emitted from the sample; and, at least two linear arrays disposed about the sample holder, each linear array comprising a plurality of optical fibers having a first end and a second end, wherein the first ends of the fibers are disposed along the length of the container and in proximity thereto; the second ends of the fibers of each array are bundled together to form a single end port; and the plurality of optical fibers receives the signal and transmits the signal from the first ends of the fibers to the end port comprising the second ends of the fibers; and an end port assembly optically coupled to the single end port and to a detector.

According to another embodiment of the present invention, a system is provided for detecting the presence of an analyte of interest in a sample, said system comprising an elongated, transparent container for a sample; an excitation source in optical communication with the sample, wherein radiation from the excitation source is directed along the length of the sample, and wherein the radiation induces a fluorescent signal which is emitted from the sample; and, at least four linear arrays disposed about the sample holder in a planar array, and wherein adjacent linear arrays are oriented 90 degrees with respect to each other, each linear array comprising a plurality of optical fibers having a first end and a second end, wherein the first ends of the fibers are disposed along the length of the container and in proximity thereto; the second ends of the fibers of each array are bundled together to form a single end port; and the plurality of optical fibers receives the signal and transmits the signal from the first ends of the fibers to the end port comprising the second ends of the fibers; and an end port assembly optically coupled to the single end port and to a detector, wherein the end port assembly comprises at least one lens.

According to another embodiment of the present invention, a method for detecting the presence of an analyte of interest in a sample is provided, said method comprising providing an elongated, transparent container for a sample; providing an excitation source in optical communication with the sample, wherein radiation from the excitation source is directed along the length of the sample, and wherein the radiation induces a signal which is emitted from the sample; and providing at least two linear arrays disposed about the sample holder, each linear array comprising a plurality of optical fibers having a first end and a second end, wherein the first ends of the fibers are disposed along the length of the container and in proximity thereto; the second ends of the fibers of each array are bundled together to form a single end port; the plurality of optical fibers receives the signal and transmits the signal from the first ends of the fibers to the end port comprising the second ends of the fibers; and an end port assembly optically coupled to the single end port and to a detector.

According to yet another embodiment of the present invention, a method is provided for detecting the presence of an analyte of interest in a sample, said method comprising providing an elongated, transparent container for a sample; providing an excitation source in optical communication with the sample, wherein radiation from the excitation source is directed along the length of the sample, and wherein the radiation induces a fluorescent signal which is emitted from the sample; and, providing at least four linear arrays disposed about the sample holder in a planar array, and wherein adjacent linear arrays are oriented 90 degrees with respect to each other, each linear array comprising a plurality of optical fibers having a first end and a second end, wherein the first ends of the fibers are disposed along the length of the container and in proximity thereto; the second ends of the fibers of each array are bundled together to form a single end port; the plurality of optical fibers receives the signal and transmits the signal from the first ends of the fibers to the end port comprising the second ends of the fibers; and providing an end port assembly optically coupled to the single end port and to a detector, wherein the end port assembly comprises at least one lens.

DETAILED DESCRIPTION

The present invention describes a system for detecting the presence of an analyte of interest in a sample. The analyte of interest may be biological or chemical in nature, and by way of example only may include chemical moieties (toxins, metabolites, drugs and drug residues), peptides, proteins, cellular components, viruses, and combinations thereof. The analyte of interest may be in either a fluid or a supporting media such as, for example, a gel. In one embodiment, the analyte of interest is a prion, a conformationally altered form ($PrP^{Sc}$) of cellular prion protein ($PrP^{C}$), which has distinct physiochemical and biochemical properties such as aggregation, insolubility, protease digestion resistance, and a β-sheet-rich secondary structure. Herein, "prion" is understood to mean the abnormal isoform (e.g., $PrP^{Sc}$) of a proteinaceous, infectious agent implicated in causing transmissible spongiform encephalopathies (TSE's) or prion diseases, understood herein to include but are not limited to, the human diseases Creutzfeldt-Jakob disease (CJD), Gerstmann-Sträussler-Scheinker syndrome (GSS), fatal familial insomnia (FFI), and kuru, as well as the animal forms of the disease: bovine spongiform encephalopathy (BSE, commonly known as mad cow disease), chronic wasting disease (CWD) (in elk and deer), and scrapie (in sheep). It is to be understood that "proteinaceous" means that the prion may comprise proteins as well as other biochemical entities, and thus is not intended to imply that the prion is comprised solely of protein.

Figure 3:
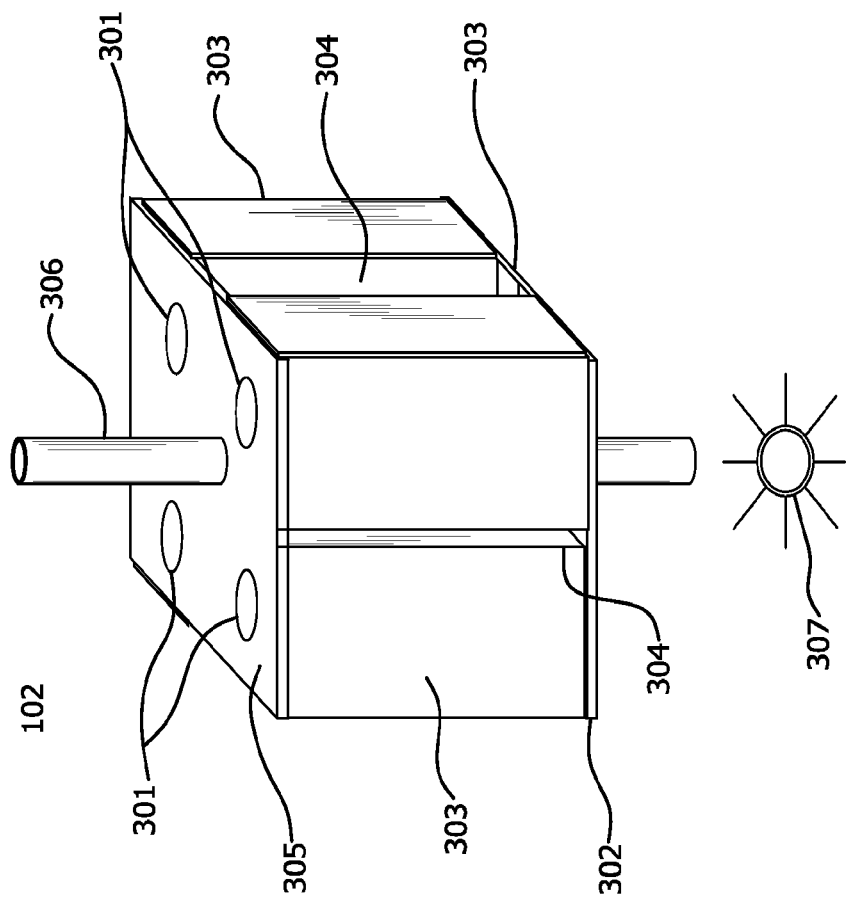
FIG. 3 is a schematic representation of one embodiment of a sample container of the present invention.
Figure 4:
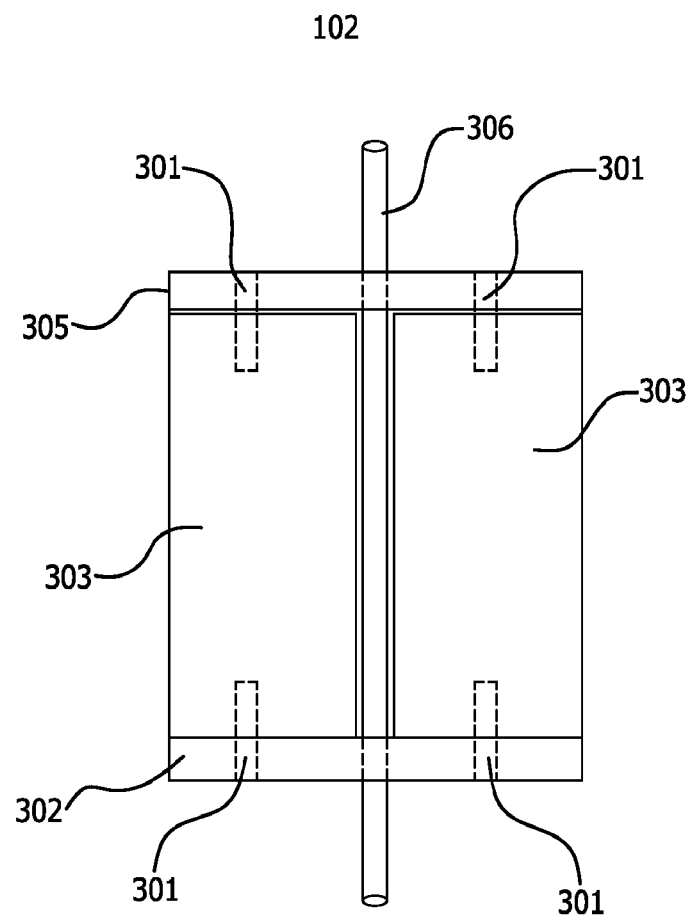
FIG. 4 is a schematic representation of the sample container of FIG. 3, as viewed from one side.
Figure 5:
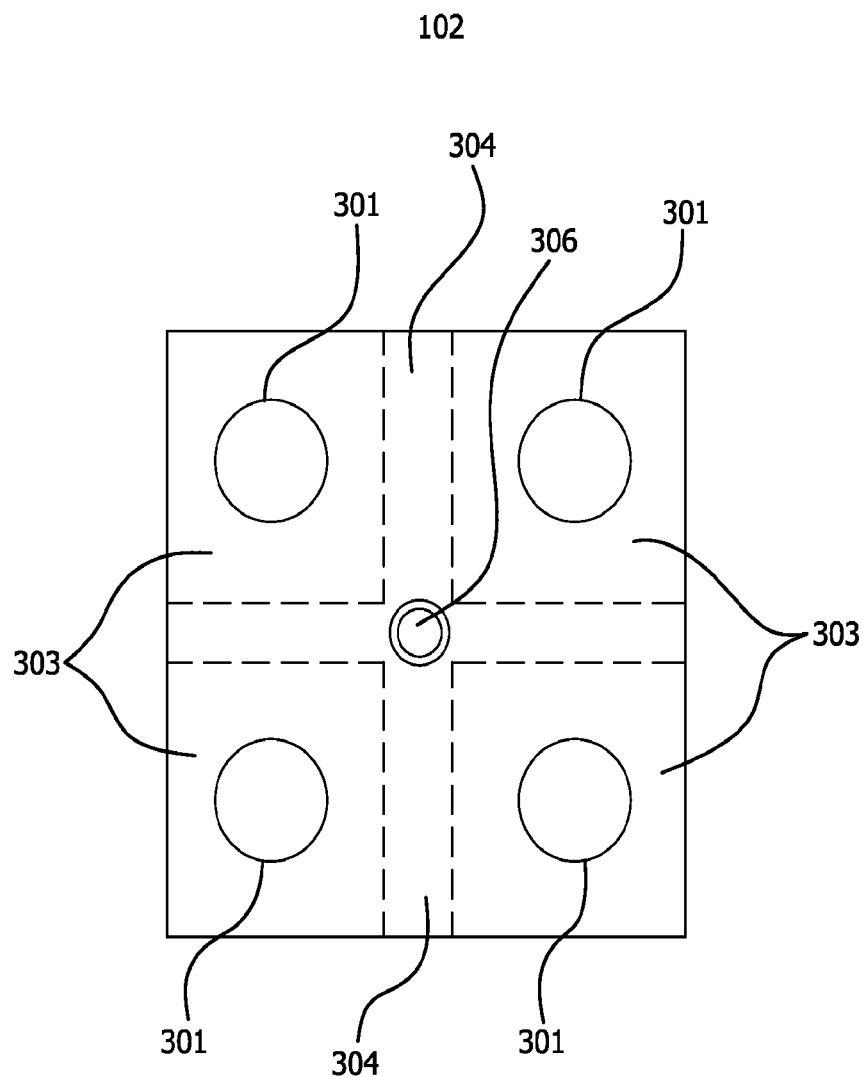
FIG. 5 is a schematic representation of the sample container of FIG. 3, as viewed from the top.

The sample is irradiated by an excitation source in optical communication with the sample 307 (FIG. 3). The radiation from the excitation source may be directed along the length of the sample. The excitation source may include, but is not limited to, a laser, a flash lamp, an arc lamp, a light emitting diode, or the like. Preferably, the excitation source is a laser. One non-limiting example of a suitable laser is a 532 nm, frequency doubled Nd:YAG laser. Irradiation of the sample causes the sample to emit a signal. The signal may be selected from the group consisting of fluorescence, phosphorescence, ultraviolet radiation, visible radiation, infrared radiation, Raman scattering, and combinations thereof. In one embodiment, the signal is a fluorescence signal. The emitted signal may be correlated to the concentration of the analyte in the sample by methods that would be readily apparent to one of skill in the art.

Figure 1:
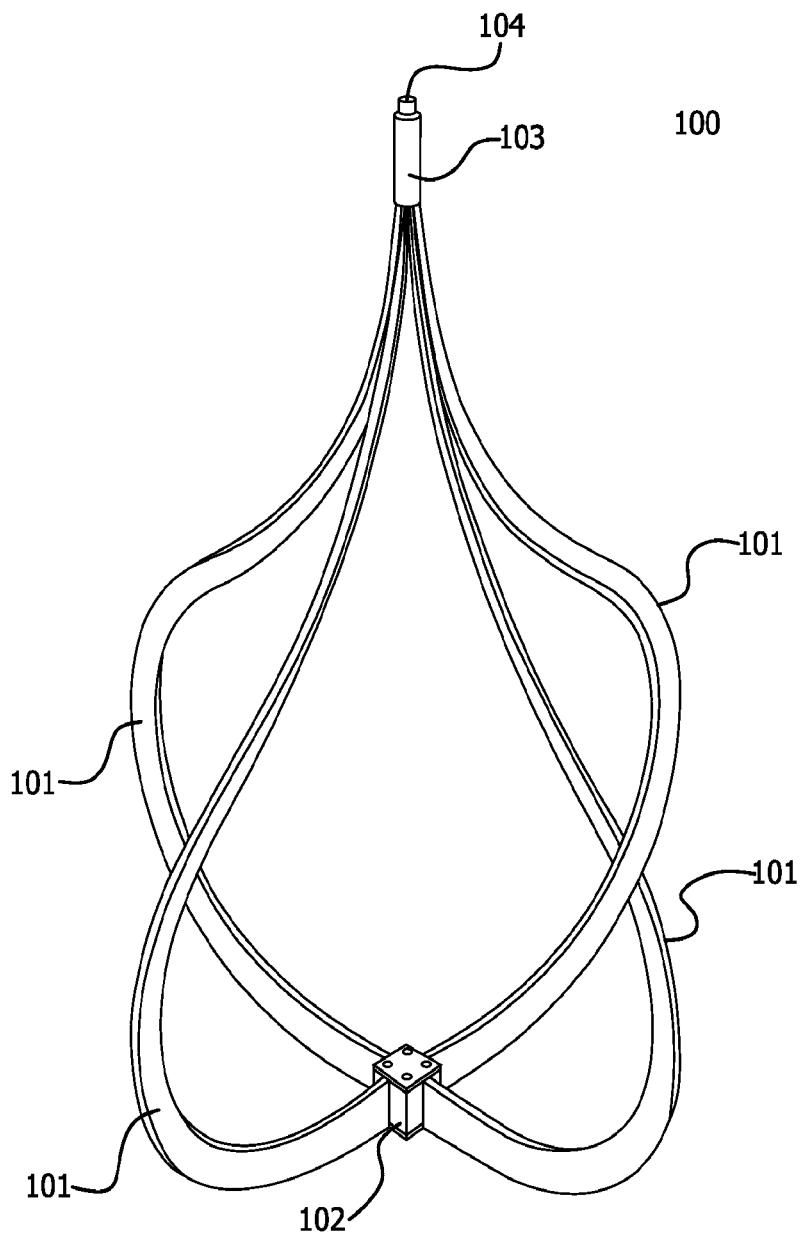
FIG. 1 is a schematic representation showing one embodiment of the system of the present invention.

FIG. 1 depicts the system 100 of the present invention. In this embodiment, four linear arrays 101 extend from a sample holder 102, which houses an elongated, transparent sample container 306, to an end port 103. The distal end of the endport 104 is inserted into an end port assembly 200. The linear arrays comprise a plurality of optical fibers having a first end and a second end, the plurality of optical fibers optionally surrounded by a protective and/or insulating sheath. The number of fibers may vary, and in one embodiment is from about 10 to about 100, alternatively is from about 25 to about 75, and alternatively is about 50. The number of linear arrays may vary, and is at least two. The maximum number of linear arrays is dependent upon the size of the sample holder in that the sample holder must be large enough to afford sufficient space for the first ends of the optical fibers to surround and be in close proximity (e.g., from about 1 mm to about 1 cm) to a sample container. In one embodiment, the number of linear arrays is from 2 to 10, alternatively is from about 4 to 6, and alternatively is 4. In one embodiment, the linear arrays are disposed in a planar array, wherein the adjacent linear arrays are oriented equidistantly from one another and surrounding the sample holder. When the number of linear arrays is four, the adjacent linear arrays are oriented at 90 degree angles with respect to each other. The length of the linear array may vary widely and is dependent upon the number and nature of the optical fibers. The length must be sufficient to allow bundling of the optical fibers from each linear array without compromising the integrity of the optical fibers. In principle, there is no upper limit on the length of the optical fibers, which would allow for a sample to be located remotely from the diagnostic equipment used to analyze the sample.

The first ends of the optical fibers may be disposed in a substantially linear manner along the length of the container comprising the sample. The second ends of the optical fibers are bundled together to form a single end port. In other words, a given length of the second ends of the fibers from each linear array are intermingled to form a single bundle. Preferably, the second ends of the fibers from each linear array are randomly interspersed within the bundle. The plurality of optical fibers receives the signal emitted from the analyte of interest and transmits the signal from the first ends of the fibers to the end port comprising the second ends of the fibers. The fibers have a high numerical aperture (NA), which corresponds sine θ/2, where θ is the angle of accepted incident light (optical acceptance angle). In the present invention, the NA may range from about 0.20 to about 0.25 and the optical acceptance angle of from about 20 degrees to about 45 degrees. The optical acceptance angle is chosen such that substantially all of the emitted signal may be intercepted by the plurality of fibers. This ensures optimum collection efficiency of the signal from dilute analytes, such as $PrP^{sc}$.

In one embodiment, the optical fibers comprise fused silica. The fibers may have a diameter of from about 50 micrometers to about 400 micrometers. The bundling of the optical fibers from each linear array offers several advantages. Rather than separate detectors for each linear array being required, a single detector may be used. For a system comprising four linear arrays, this results in a detection area having one-quarter the size of four individual detectors. The background noise thus is dramatically decreased, which in turn increases the signal to noise ratio and thus lowers the limit of detection. In one embodiment, the size of the detector is from about 0.5 mm×0.5 mm to about 1 mm×1 mm. The limit of detection of the system of the present invention is at least 0.1 attomole of analyte, alternatively is at least 200 attomole, alternatively is from about 0.1 attomole to about 1.0 micromole, alternatively is from about 0.1 attomole to about 1 nanomole, and alternatively is from about 0.4 to about 1.0 attomole of analyte. Alternatively, the limit of detection of the system is at least 0.1 attogram of analyte, and alternatively is at least 10 attogram of analyte.

Figure 2:
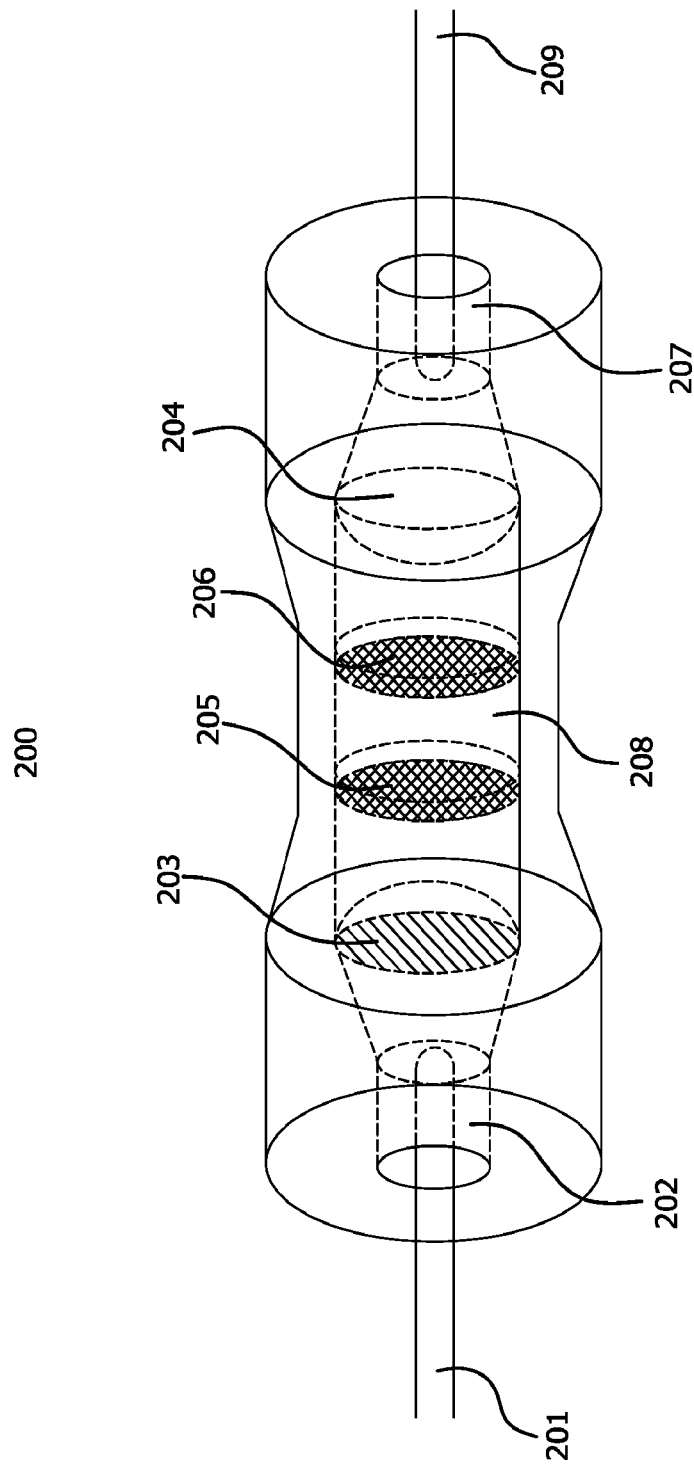
FIG. 2 is a schematic representation showing a side view of one embodiment of an end port assembly of the present invention.

FIG. 2 depicts one embodiment of an endport assembly of the present invention. The distal end of the single endport 104 comprising the bundled optical fibers is inserted into the entrance 202 of endport assembly 200. The signal is transmitted by the optical fibers through the endport assembly 200 to the exit 207, and is then transmitted to outgoing optical fiber 208 which in turn is in contact with a detector. Outgoing optical fiber 208 may have a diameter of from about 300 microns to about 500 microns, and preferably is about 400 microns. Therefore, the end port assembly optically couples the single end port to the detector. The endport assembly may comprise a first lens 203, which serves to collimate the incident signal. The endport assembly further may comprise a second lens 204, which serves to focus the outgoing signal to a NA suitable for outgoing optical fiber 208. The endport assembly further may comprise at least one notch filter 205 and at least one bandpass filter 206.

Non-limiting examples of suitable detectors include photodiode detectors, photo-multipliers, charge-coupled devices, a photon-counting apparatus, optical spectrometers, and any combination thereof.

FIG. 3 depicts one embodiment of a suitable sample holder 102 of the present invention. Spacers 303 are positioned such as to provide a space for an elongated, transparent container 306 to pass through the sample holder 300. In one embodiment, the sample holder 300 is a capillary, and may be made of glass, quartz, or any other suitable material that would be known to one of skill in the art. By way of example only, the capillary may hold 100 microliters of fluid. Spacers 303 further are positioned to provide a slot 304, or space, for the first ends of the optical fibers to surround and be in close proximity to the transparent container. Spacers 302 are held in place by top end plate 305 and bottom end plate 302, both of which are attached to the spacers 303 by a means for fastening 301, such as a screw.

Another advantage of the system of the present invention is that no external power source, other than that required to power the laser, is required to collect and detect the signal emitted from the analyte of interest. This simplifies the system, increases portability and thus the range of applications. In addition, the absence of an external power source significantly further reduces the amount of background noise that must be overcome, which in turn contributes to a lower limit of detection.

The emitted signal that is captured is converted to an electrical signal by photo-detector and transmitted to an analyzer (not shown), which receives the electrical signal and analyses the sample for the presence of the analyte. Examples of analyzers would be well-understood by those of skill in the art. The analyzer may include a lock-in amplifier, which enables phase sensitive detection of the electrical signal, or any other means known in the art for analyzing electric signals generated by the different types of photo-detectors described herein.

Example 1

The sample is excited by focusing temporally modulated light from a solid state, frequency-doubled Nd:YAG laser (Beam of Light Tech.™, Clackamas, Oreg.) along the axis of the capillary, with typical power of 30 mW continuous wave at a wavelength of 532 nm, which matches well with the absorption peak of reference material rhodamine. A fiber optic assembly was designed comprised of four linear arrays which span approximately a third of the length of the capillary and are positioned at 90 degrees with respect to each other around the perimeter of the capillary. Because of the large numerical aperture (0.22, or an acceptance angle of ~23 deg.) of the fibers, this orientation of the fibers results in complete coverage of the sample's field of view. The light collected by the four linear arrays is ganged (i.e., bundled, or combined) and focused into transfer optics in which a holographic notch filter (Kaiser Optical Systems Inc. Ann Arbor, Mich.), and band pass filters (Omega Optical, Inc. Brattleboro, Vt.) are mounted. These are used to eliminate the scattered light from the excitation source, and band-limit the detection of the fluorescence of the reporter dye, respectively. The light is then focused back into a single, multi-mode, 400 micron optical fiber (Thorlabs™, Inc. Newton, N.J.) and coupled to a single low noise photo-voltaic diode detector (United Detector Technology, Hawthorne, Calif.) which is mounted on a BNC connector directly on the pre-amplifier of the detection electronics. Detection of the signal employs a phase sensitive, or "lock-in", detection scheme. The excitation source is modulated with an optical chopper (Thorlabs Inc.) which serves to generate the reference frequency for the detection system. The diode detector is mounted on the input of the transconductance pre-amplifier (Stanford Research Systems, Inc. Sunnyvale, Calif.) to reduce the total line impedance and eliminate difficulties in impedance matching of the signal at these low levels. The signal is then detected with a lock-in amplifier (Stanford Research Systems) and data acquisition is performed through a LabView™ (National Instruments Inc., Austin, Tex.) program. The program consists of an electronic strip chart which poles the lock-in amplifier for its reading in voltage and periodically displays the time history of the measurements to the operator, and stores the values with a time stamp in an ASCII file. The time constant of the lock-in amplifier should be chosen to provide a bandwidth of a few tenths of a Hertz. For the measurements, a time constant of 3 seconds was chosen. The lock-in requires several time constants in duration to obtain a stable reading (3 to 30 seconds in this case). The values for the measurements were taken after the signal had stabilized (20 to 30 sec.) after loading a new sample. The modulation of the excitation source, and reference frequency for the lock-in detector, were 753 Hz which was chosen to minimize environmental noise. In addition to this filtering of the signal at line-frequency and two times line frequency was done with the lock-in amplifier and the pre-amplifier signal was band-pass filtered at the modulation frequency. For the samples the pre-amplifier sensitivity of 1 nAN was chosen, giving an input impedance of 1 M Ohm. In making the measurements we maintained a set of startup procedures which included: a warm up of 15 minutes for all electronics (the laser, lock-in amplifier, pre-amplifier), a visual check of dark signal levels to assure that system is properly electrically grounded, a measurement of laser power to check for stability and output level, a visual check of laser alignment. Control measurement of baseline signal is checked using a capillary with distilled, deionized water.

The sensitivity limits of the instrument were tested by measuring the fluorescence signal emission of Rhodamine Red at decreasing concentrations. Rhodamine Red was detectable to a concentration of 0.01 attograms (ag) [20 attomoles (am)]. Determination of specificity and sensitivity was carried out by performing assays using full-length recombinant PrP (rPrP) from deer, hamster, mouse and sheep. Regardless of the species tested, the limits of detectability were ≥10 ag PrP.

Brain homogenates from normal and infected hamsters, deer and sheep were examined for their use in the method of the present invention. Western blotting of 10% brain homogenates confirmed the presence of $PrP^{Sc}$ in the starting material. Typical PrP banding patterns were evident in the 10% brain homogenates prior to PK treatment with the characteristic band shifting to lower molecular sizes of $PrP^{Sc}$ following PK digestion along with the elimination of $PrP^{C}$ from the normal hamster brain material as confirmation of complete proteolytic digestion. Serial dilutions of detergent extracted brain homogenates from clinical animals have demonstrated that the limits of $PrP^{Sc}$ detection by Western blotting is approximately $10^{-3}$-$10^{-4}$ while detection of $PrP^{Sc}$ by capture enzyme-linked immunosorbent assay (ELISA) was sensitive following an additional $10^{1}$-$10^{2}$ fold dilution (data not shown). In comparison, using the same monoclonal antibodies (Mabs) and brain homogenates, the sensitivity of the assay reported in this manuscript exceeded that for Western blotting and capture ELISA by at least 5 orders of magnitude. Using the method of the present invention, the signal to baseline ratios (S/B) were used to evaluate PrP detectability in brain homogenates. It was determined that an S/B ratio of greater than 1.1 indicated the presence of PrP. Serial dilutions of PK-treated and untreated brain homogenates from normal and infected brain tissue of hamsters, sheep and deer were assayed by SOFIA. As expected, following PK treatment all samples from normal brain tissues had S/B ratios of less than 1.1 regardless of the concentration tested indicating the absence of $PrP^{C}$. As demonstrated by total signal output or S/B ratios above 1.1, protease resistant $PrP^{Sc}$, from serial 10-fold dilutions of PK-treated infected hamster brain homogenates, was detectable to a dilution of $10^{-11}$ and from sheep and deer to $10^{-10}$. In addition, maximum $PrP^{Sc}$ detection from the PK-treated brain homogenates ranged from dilutions of $10^{-7}$-$10^{-8}$ for hamsters as well as sheep and deer.

In the case of 10-fold serially diluted non-PK treated normal brain homogenates, $PrP^{C}$ was detectable by SOFIA to a dilution of $10^{-11}$ for hamsters and $10^{-10}$ for deer and sheep (with peak detection at $10^{-6}$-$10^{-7}$ dilutions) after which the S/B ratios all fell below 1.1. The S/B ratios from of non-PK treated brain tissue of 263K infected hamsters, scrapie-infected sheep and CWD-infected deer continued to indicate the presence of PrP. Serially diluted brain homogenates from infected tissues all showed S/B values greater than 1.1 to a dilution of $10^{-11}$ for sheep and deer (with peak detection at $10^{-7}$) and $10^{-13}$ for hamsters (peak detection at $10^{-8}$). These results indicate that PrP from non-protease treated, infected brain tissue can be diluted beyond the levels of $PrP^{C}$ detectability while still maintaining the capability to detect total $PrP^{Sc}$. These results further suggest that there is at least 1 log more total $PrP^{Sc}$ than $PrP^{C}$ in an infected brain at clinical disease. In support of this, it has previously been reported that $PrP^{Sc}$ accumulates in the brain during scrapie infection and attains concentrations 10 times greater than that of $PrP^{C}$. Using previously published data on 263K-infected hamsters (R. Atarashi et al. "Ultrasensitive detection of scrapie prion protein using seeded conversion of recombinant prion protein," Nature Meth. vol. 4 (2007) pp. 645-650), SOFIA has a detection limit of approximately 10 ag of $PrP^{Sc}$ from non-PK treated hamster brain. Extrapolation directly from the hamster data suggests that 1 femtogram of $PrP^{Sc}$ can be detected from sheep and deer brain material. However, assuming equal antibody reactivity, Western blotting of diluted samples indicated that there is at least 10-100 fold more $PrP^{Sc}$ in hamster brains than in sheep and deer brain material on a gram equivalent basis (data not shown) suggesting that detection of the protein in the latter two species could be in the range of 10-100 ag or better.

In all embodiments of the present invention, all percentages are by weight of the total composition, unless specifically stated otherwise. All ratios are weight ratios, unless specifically stated otherwise. All ranges are inclusive and combinable. All numerical amounts are understood to be modified by the word "about" unless otherwise specifically indicated.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

Whereas particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A system for detecting the presence of an analyte of interest in a sample, said system comprising:

a) an elongated, transparent container for a sample;

b) an excitation source in optical communication with the sample, wherein radiation from the excitation source is directed along the length of the sample, and wherein the radiation induces a signal which is emitted from the sample; and, c) at least two linear arrays disposed about the container, each linear array comprising a plurality of optical fibers having a first end and a second end, wherein:

i the first ends of the fibers are disposed along the length of the container and in proximity thereto;

ii the second ends of the fibers of each array are bundled together to form a single end port;

iii the plurality of optical fibers receives the signal and transmits the signal from the first ends of the fibers to the end port comprising the second ends of the fibers; and d) an end port assembly optically coupled to the single end port and to a detector.

2. The system according to claim 1, wherein the end port assembly further comprises at least one lens.

3. The system of claim 1, wherein the end port assembly further comprises a notch filter.

4. The system of claim 1 wherein the end port assembly further comprises a bandpass filter.

5. The system of claim 1, wherein the system comprises four linear arrays.

6. The system of claim 5, wherein the linear arrays are arranged in a planar array, and wherein adjacent linear arrays are oriented 90 degrees with respect to each other.

7. The system of claim 1, wherein the excitation source is a laser.

8. The system of claim 1, wherein the signal is selected from the group consisting of fluorescence, phosphorescence, ultraviolet radiation, visible radiation, infrared radiation, Raman scattering, and combinations thereof.

9. The system of claim 1, wherein the second ends of the fibers of each array are bundled together in a random order.

10. The system of claim 1, wherein the detector has a size of from 0.5 mm×0.5 mm to 1 mm×1 mm.

11. The system of claim 1, wherein each linear array comprises from 10 to 100 fibers.

12. The system of claim 1, wherein the optical fibers have an optical acceptance angle of from 20 degrees to 45 degrees.

* * * * *